(12) United States Patent
Bornzin et al.

(10) Patent No.: US 7,505,814 B2
(45) Date of Patent: Mar. 17, 2009

(54) SYSTEM AND METHOD FOR EVALUATING HEART FAILURE BASED ON VENTRICULAR END-DIASTOLIC VOLUME USING AN IMPLANTABLE MEDICAL DEVICE

(75) Inventors: Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 688 days.

(21) Appl. No.: 10/810,437

(22) Filed: Mar. 26, 2004

(65) Prior Publication Data
US 2005/0215914 A1     Sep. 29, 2005

(51) Int. Cl.
*A61N 1/08* (2006.01)
*A61B 5/053* (2006.01)

(52) U.S. Cl. ........................... 607/17; 600/547

(58) Field of Classification Search ............ 607/4–6, 607/9, 17–18, 24–25; 600/508–509, 513, 600/521, 526, 547
See application file for complete search history.

(56) References Cited

U.S. PATENT DOCUMENTS

| | | | | |
|---|---|---|---|---|
| 4,291,699 | A | 9/1981 | Geddes et al. | 178/419 D |
| 4,674,518 | A | 6/1987 | Salo | 128/695 |
| 5,154,171 | A * | 10/1992 | Chirife | 607/24 |
| 5,174,286 | A * | 12/1992 | Chirife | 607/11 |
| 5,328,460 | A | 7/1994 | Lord et al. | 604/67 |
| 5,643,327 | A | 7/1997 | Dawson et al. | 607/24 |
| 5,800,467 | A * | 9/1998 | Park et al. | 607/17 |
| 5,861,008 | A | 1/1999 | Obel et al. | 607/11 |
| 5,957,861 | A | 9/1999 | Combs et al. | 600/547 |
| 6,070,100 | A * | 5/2000 | Bakels et al. | 607/9 |
| 6,119,040 | A * | 9/2000 | Chirife | 607/18 |
| 6,278,894 | B1 * | 8/2001 | Salo et al. | 600/547 |
| 6,314,322 | B1 | 11/2001 | Rosenberg | 607/17 |
| 6,336,903 | B1 * | 1/2002 | Bardy | 600/508 |
| 6,409,675 | B1 | 6/2002 | Turcott | 600/508 |
| 6,438,408 | B1 | 8/2002 | Mulligan et al. | 600/510 |
| 6,494,832 | B1 | 12/2002 | Feldman et al. | 600/301 |
| 6,512,949 | B1 | 1/2003 | Combs et al. | 600/547 |
| 6,512,952 | B2 | 1/2003 | Stahmann et al. | 607/9 |
| 6,572,557 | B2 | 6/2003 | Tchou et al. | 600/483 |
| 6,622,045 | B2 | 9/2003 | Snell et al. | 607/30 |
| 6,628,988 | B2 | 9/2003 | Kramer et al. | 607/9 |
| 6,643,546 | B2 | 11/2003 | Mathis et al. | 607/9 |

(Continued)

FOREIGN PATENT DOCUMENTS

EP    0347708 A1    12/1989

(Continued)

*Primary Examiner*—Carl H Layno
*Assistant Examiner*—Jessica Reidel

(57) ABSTRACT

Briefly, values representative of ventricular end-diastolic volume (EDV) are detected using ventricular electrodes and then heart failure, if occurring within the patient, is evaluated based on ventricular EDV. In this manner, ventricular EDV is used as a proxy for ventricular end-diastolic pressure. By using ventricular EDV instead of ventricular end-diastolic pressure, heart failure is detected and evaluated without requiring sophisticated sensors or complex algorithms. Instead, ventricular EDV is easily and reliably measured using impedance signals sensed by implanted ventricular pacing/sensing electrodes. The severity of heart failure is also evaluated based on ventricular EDV values and heart failure progression is tracked based on changes, if any, in ventricular EDV values over time.

26 Claims, 11 Drawing Sheets

U.S. PATENT DOCUMENTS

| | | |
|---|---|---|
| 6,645,153 B2 | 11/2003 | Kroll et al. .................. 600/481 |
| 6,711,439 B1 | 3/2004 | Bradley et al. ................. 607/6 |
| 7,171,258 B2 * | 1/2007 | Goode ........................ 600/509 |
| 2002/0002389 A1 | 1/2002 | Bradley et al. ................. 607/8 |
| 2002/0115939 A1 | 8/2002 | Mulligan et al. ............ 600/510 |
| 2002/0151938 A1 * | 10/2002 | Corbucci ..................... 607/25 |
| 2002/0161410 A1 * | 10/2002 | Kramer et al. ................. 607/9 |
| 2003/0055461 A1 | 3/2003 | Girouard et al. .............. 607/17 |
| 2003/0074029 A1 | 4/2003 | Deno et al. ................... 607/23 |
| 2004/0002741 A1 * | 1/2004 | Weinberg ..................... 607/17 |
| 2005/0080460 A1 * | 4/2005 | Wang et al. ................... 607/17 |
| 2005/0203429 A1 * | 9/2005 | Judy .......................... 600/508 |

FOREIGN PATENT DOCUMENTS

| | | |
|---|---|---|
| WO | WO 99/44680 | 9/1999 |

* cited by examiner

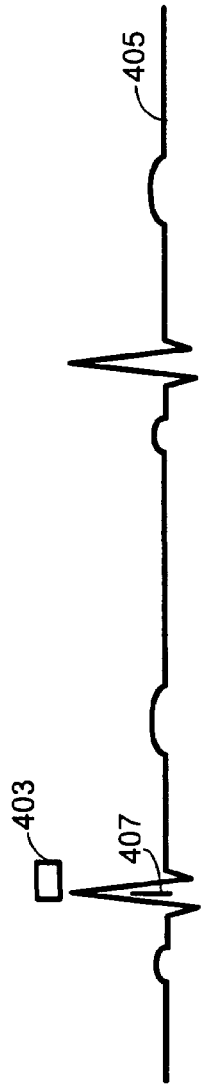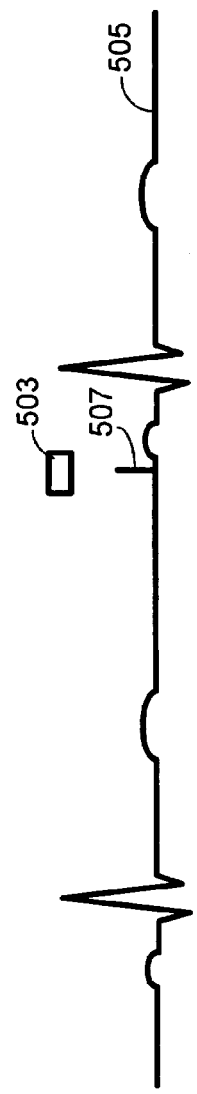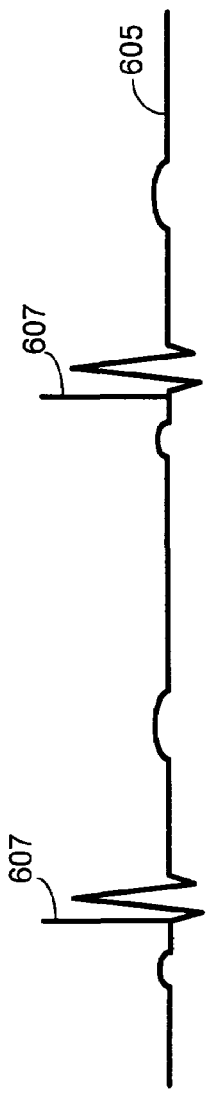

SYSTEM AND METHOD FOR EVALUATING HEART FAILURE BASED ON VENTRICULAR END-DIASTOLIC VOLUME USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for evaluating the progression of heart failure within a patient in which a medical device is implanted.

BACKGROUND

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus And Method For Treatment Of Congestive Heart Failure"; U.S. Pat. No. 6,628,988 to Kramer et al., entitled "Apparatus And Method For Reversal Of Myocardial Remodeling With Electrical Stimulation"; and U.S. Pat. No. 6,512,952 to Stahmann et al., entitled "Method And Apparatus For Maintaining Synchronized Pacing", which are incorporated by reference herein.

In view of the potential severity of heart failure, it is highly desirable to detect its onset within a patient and to track its progression or regression so that appropriate therapy can be provided. Many patients suffering heart failure already have pacemakers or ICDs implanted therein or are candidates for such devices. Accordingly, it is desirable to provide such devices with the capability to automatically detect and track heart failure and, heretofore, a number of attempts have been made to provide for monitoring of physiological parameters associated with heart failure using implantable cardiac devices in conjunction with physiological sensors.

For example, U.S. Pat. No. 6,572,557, to Tchou et al., entitled "System and Method for Monitoring Progression of Cardiac Disease State Using Physiologic Sensors", describes a technique for monitoring physiological parameters associated with the progression, stabilization, or regression of symptoms of heart disease such as CHF. The monitoring is implemented by ongoing surrogate measurement of standard and direct measurements, such as daily activity and respiratory and cardiac rate response, utilizing existing implantable, rate-responsive stimulation devices that incorporate activity, respiration, and/or other sensors. The system includes a sensor that measures activity and/or minute ventilation when triggered by changes in the sensed intrinsic heart rate and/or changes in a sensor-indicated pacing rate.

U.S. Pat. No. 6,645,153, to Kroll et al., entitled "System And Method For Evaluating Risk Of Mortality Due To Congestive Heart Failure Using Physiologic Sensors", describes a technique for determining a CHF mortality risk metric based on a combination of estimated ventilatory response values and the slope of heart rate reserve as a function of predicted heart rates. Ventilatory response is estimated based on detected values of actual heart rate, arterial oxygen saturation, right ventricular oxygen, stroke volume, tidal volume, and respiration rate. Heart rate reserve values are derived from the actual heart rate along with patient age and rest heart rate. The predicted heart rates, which represent the heart rates the patient would achieve if healthy, are derived from activity sensor signals. The CHF mortality risk metric is then calculated as a ratio of ventilatory response and the slope of the heart rate reserve.

U.S. Pat. No. 6,438,408 to Mulligan et al., entitled "Implantable Medical Device For Monitoring Congestive Heart Failure", sets forth a technique for evaluating CHF that measures a group of parameters indicative of the state heart failure by employing electrocardiogram (EGM) signals, blood pressure (including absolute pressure, developed pressure, and change in pressure with time), and heart chamber volumes, specifically end systolic volumes (ESV). Based upon these signals, the technique operates to generate sets of parameters including (1) a relaxation or contraction time constant; (2) a mechanical restitution value; (3) a recirculation fraction value; and (4) an end systolic elastance value, indicative of the ratio of end systolic blood pressure to end systolic volume. Then, based upon a combination of these parameters, the system seeks to track changes in a heart failure with time.

A significant problem with many of the aforementioned techniques is their complexity. In many cases, multiple sensors are required for detecting multiple signals, which are then combined using fairly complex algorithms in an attempt to evaluate and track heart failure. It would be desirable to instead provide an effective but much more straightforward technique for evaluating heart failure, which does not require special sensors or complex algorithms. In addition, at least insofar as the techniques of Mulligan et al. are concerned, which operate to detect ESV (among many other parameters), it is believed that ESV and parameters derived therefrom are not as reliable an indicator of heart failure as would be preferred. In contrast, it has been recognized that left ventricular end-diastolic pressure, alone or in combination with other parameters, is a more effective parameter for use in tracking heart failure. However, there are technical challenges to the reliable detection of left ventricular end-diastolic pressure and so techniques exploiting left ventricular end-diastolic pressure have, heretofore, not been effectively implemented.

Accordingly, it would be desirable to provide an alternative technique for evaluating and tracking heart failure, which instead uses a proxy for left ventricular end-diastolic pressure, so that end-diastolic pressure itself need not be detected. In particular, it is desirable that a proxy for left ventricular end-diastolic pressure be provided that can be detected without additional or complicated sensors and that can instead exploit conventional pacing electrodes implanted with the heart. It is to this end that aspects of invention are directed.

SUMMARY

In accordance with one illustrative embodiment, techniques are provided for evaluating heart failure within a patient using an implantable medical device. Briefly, values representative of ventricular end-diastolic volume (EDV) are detected and then heart failure, if occurring within the patient, is detected based on the values representative of ventricular EDV. Hence, with this technique, ventricular EDV is generally used as a proxy or surrogate for ventricular end-diastolic pressure. By using ventricular EDV instead of ventricular end-diastolic pressure, heart failure can be detected and evaluated without requiring sophisticated sensors or complex algorithms. In particular, ventricular EDV can be easily and reliably measured using impedance signals sensed by implanted ventricular pacing/sensing electrodes. The severity of heart failure can also be evaluated based on ventricular EDV values and heart failure progression can be tracked based on changes, if any, in ventricular EDV values over time.

Herein, the term ventricular EDV generally refers to any suitable measure of ventricular filling occurring between beats when the ventricles are at their fullest and may be detected, e.g., based upon measurements of right ventricular EDV values, left ventricular EDV values or combined right and left ventricular EDV values The value for EDV, which represents the sum of the active and passive filling volumes, may be measured during the pre-ejection interval subsequent to a ventricular depolarization, or during delivery of a ventricular pacing pulse (i.e. a V-pulse.) Moreover, the gradient (i.e. time rate of change) in ventricular volume is generally minimal and so a comparison in ventricular EDV from one cardiac cycle to another can be reliably performed to quantify small changes in ventricular EDV over time. Furthermore, unlike ESV and parameters derived therefrom, changes in EDV are more strongly correlated with changes in heart failure. The measurement of ventricular volume need not be obtained only at the very end of the diastolic phase of the cardiac cycle. Rather, a value of ventricular volume representative of the passive filling phase may be detected, for example, during an interval just prior to an atrial contraction. The active filling contribution of the atrium may thus be ascertained by taking the difference between the EDV and the volume measured prior to the atrial contraction.

In one example, wherein the implantable medical device is coupled to at least two electrodes implanted within the ventricles, ventricular EDV is detected by: identifying a baseline point within a cardiac cycle for detecting a value representative of ventricular EDV; detecting a signal representative of the impedance between the two ventricular electrodes at the baseline point in time; and then determining a baseline ventricular EDV based on the impedance signal detected at the point in time. Ventricular EDV values are detected at the baseline point for all cardiac cycles within at least one complete respiration cycle. The values are then processed for comparison against various stored ventricular EDV threshold values representative of the onset and severity of heart failure and for comparison against previously detected ventricular EDV values of the patient for use in tracking the progression of heart failure over time. The processing step may include averaging. By using electrodes implanted within the ventricles, the ventricular EDV is thereby determined based upon impedance values derived from an electrical field generally confined to the ventricles and hence substantially unaffected by other factors, such as fluid levels with the lungs. Moreover, by measuring the ventricular EDV only at baseline points within cardiac cycle and by averaging over at least one complete respiration cycle, variations in impedance caused by cardiac contraction or respiration are substantially eliminated so that small changes in ventricular EDV over time can be detected and tracked.

In one specific example, the baseline point within the cardiac cycle for detecting the baseline ventricular EDV is selected within a window 10-50 msecs following ventricular depolarization, i.e. within the pre-ejection interval. A detection pulse, which may have a relatively low magnitude, is applied to the ventricles at the baseline point and the ventricular impedance is derived from the detection pulse. The ventricular impedance value is then converted to a ventricular volume value. In another specific example, the baseline point is selected within a window 10-50 msecs prior to a next expected atrial depolarization. Again, a detection pulse, which may have a relatively low magnitude, is applied to the ventricles at the baseline point and the ventricular impedance is derived from the detection pulse. This is a measurement at the end of the passive filling phase. In still yet another example, ventricular impedance is derived from ventricular pacing pulses (V-pulses) so that no separate detection pulse is required, thus saving power within the device.

Once heart failure is detected, appropriate heart failure therapy is preferably provided by the implanted device, which may include CRT or drug therapy (if an implantable drug pump is provided with medication appropriate for heart failure.) If a significant change in heart failure is detected, appropriate warning signals are preferably delivered to the patient, either via an implanted warning device (if so equipped) or via an external bedside monitor. In this manner, the patient is immediately alerted to any potentially life-threatening progression in heart failure so that immediate medical attention can be sought. Diagnostic information representative of the severity and progression of heart failure is also stored for subsequent review by the physician. Suitable diagnostic information may also be displayed via the bedside monitor, if so configured, to aid in patient training, i.e. to inform the patient as to whether exercise regimes and the like are being effective or whether appropriate drug intervention, i.e. diuresis, is effective.

Thus, various techniques are provided for use with implantable medical device for detecting heart failure and for tracking its progression or regression. Other aspects, features and advantage of the invention will be apparent form the descriptions that follow.

BRIEF DESCRIPTION OF THE DRAWINGS

The above and further features, advantages and benefits of the present invention will be apparent upon consideration of the present description taken in conjunction with the accompanying drawings, in which:

FIG. 8 is a stylized diagram of the EKG of a cardiac cycle illustrating a pre-ejection interval detection widow for delivering the impedance measuring pulse of FIG. 7;

FIG. 11 is a stylized diagram of the EKG of a cardiac cycle illustrating detection widow for delivering the impedance measuring pulse of FIG. 10;

FIG. 13 is a stylized diagram of the EKG of a cardiac cycle illustrating V-pulses.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Heart Failure-Responsive System

Figure 1:
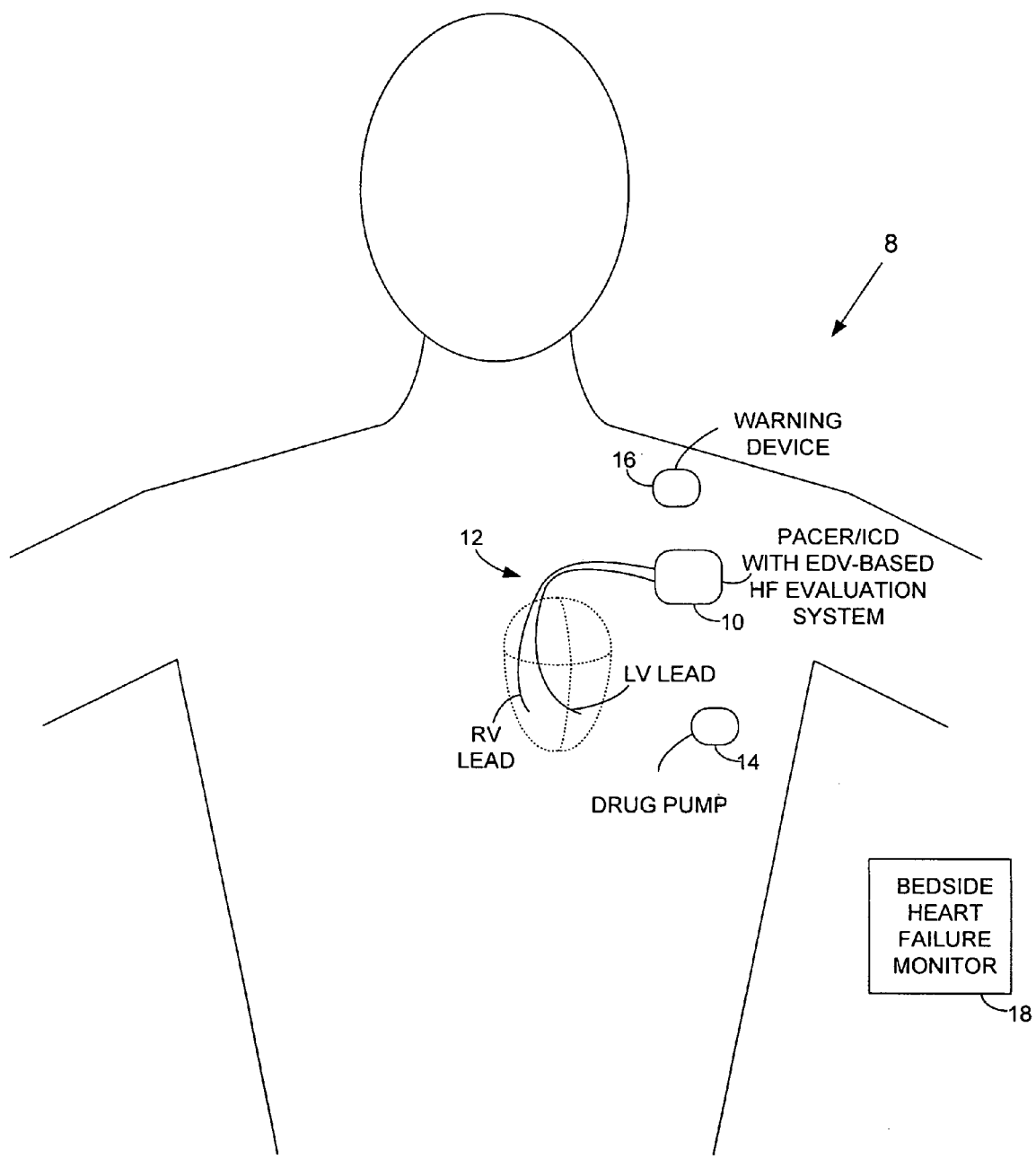
FIG. 1 illustrates pertinent components of an implantable heart failure-responsive medical system having a pacemaker or ICD capable of detecting heart failure and tracking its progression based on ventricular EDV and capable of delivering therapy or warning signals in response thereto.
Figure 4:
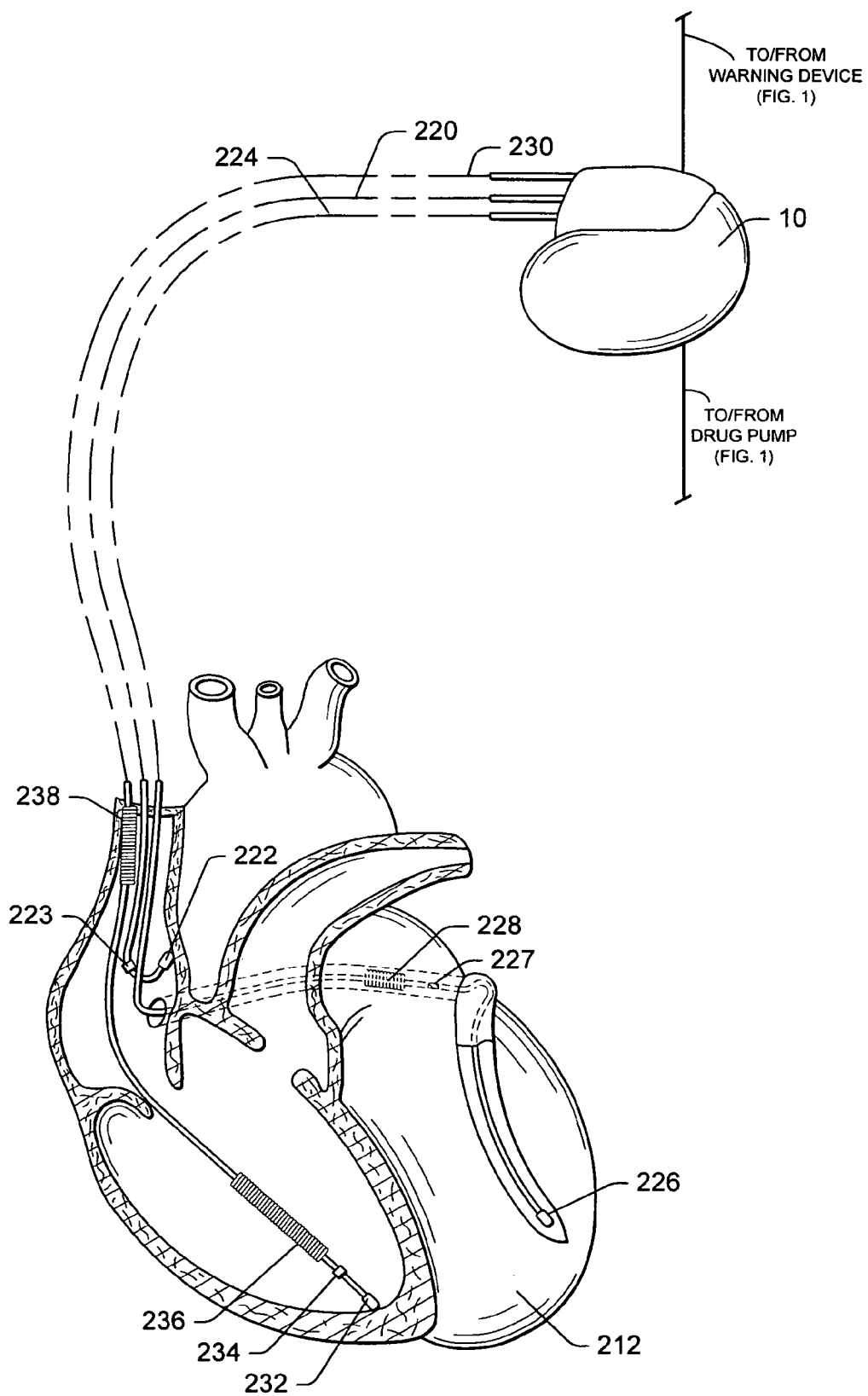
FIG. 4 is a simplified, partly cutaway view, illustrating the pacer/ICD of FIG. 1 along with at full set of leads implanted into the heart of the patient.

FIG. 1 illustrates an implantable heart failure-responsive medical system 8 capable of detecting heart failure, evaluating its severity, tracking its progression and delivering appropriate warnings and therapy. Heart failure-responsive system 8 includes a pacer/ICD 10 or other cardiac stimulation device that incorporates internal components for controlling heart failure evaluation functions (shown individually in FIGS. 5-7). More specifically, pacer/ICD 10 receives signals from at least two ventricular cardiac pacing leads 12 implanted within the heart of the patient (shown stylistically in phantom lines) from which impedance signals are derived. In FIG. 1, only ventricular pacing leads are shown. A full set of pacing leads is shown in FIG. 4. Based on the sensed impedance, the pacer/ICD determines ventricular EDV and then detects heart failure based on ventricular EDV so that appropriate therapy and warnings can be provided. The pacer/ICD also evaluates the severity of heart failure to, for example, identify the particular NYHA class of heart failure. The pacer/ICD also tracks the progression of heart failure based on any changes over time occurring in the ventricular EDV. Detailed descriptions of these techniques are set forth below.

If heart failure is detected, then appropriate therapy is automatically delivered by pacer/ICD. For example, CRT therapy may be applied using the leads implanted in the ventricles so as to improve cardiac function. Control parameters for CRT therapy are automatically adjusted based on the severity of the heart failure. Additionally, or in the alternative, the implantable heart failure-responsive system may be equipped with a drug pump 14 capable of the delivering drug therapy in an attempt to address heart failure. Discussions of possible medications for use in heart failure patients are provided below. Drug dosages provided by an implantable drug pump may be titrated based on the severity of heart failure.

Warning signals are generated using either an internal warning device 14 or an external bedside heart failure monitor 16 to notify the patient of the onset of heart failure or to advise of any significant progression thereof. Internal warning device 14 may be a vibrating device or a "tickle" voltage device that, in either case, provides perceptible stimulation to the patient to alert the patient of any significant progression of heart failure so that the patient may consult a physician. The bedside monitor may provide audible or visual alarm signals to alert the patient as well as textual or graphic displays. In addition, once heart failure has been detected, diagnostic information is stored within the pacer/ICD for subsequent transmission to an external programmer (not shown in FIG. 1) review by a physician or other medial professional. The physician may then prescribe any other appropriate therapies to address the heart failure. The physician may also adjust the operation of the pacer/ICD to activate, deactivate or otherwise control any therapies that are automatically applied. In addition, the bedside monitor may be directly networked with a centralized computing system for immediately notifying the physician of a significant increase in heart failure severity.

Hence, FIG. 1 provides an overview of an implantable system for detecting heart failure, evaluating its severity, tracking its progression and delivering appropriate therapy. Embodiments may be implemented that do not necessarily perform all of these functions. Rather, embodiments may be implemented that provide, for example, only for tracking the progression of heart failure within patients already known to have heart failure and for delivering therapy. In addition, systems provided in accordance with the invention need not include all the components shown in FIG. 1. In many cases, for example, the system will include only the pacer/ICD and its leads with heart failure therapy provided in the form of CRT. Drug pumps and warning devices are not necessarily implanted. Other implementations may employ an external monitor for generating warning signals but include no internal warning device. These are just a few exemplary embodiments. No attempt is made herein to describe all possible combinations of components that may be provided in accordance with the general principles of the invention. Also, note that, internal signal transmission lines provided for interconnecting the various implanted components are not shown in FIG. 1. Wireless signal transmission may alternatively be employed. In addition, the particular locations of the implanted components shown in FIG. 1 are merely illustrative and may not necessarily correspond to actual implant locations.

Overview of Heart Failure Evaluation Technique

Figure 2:
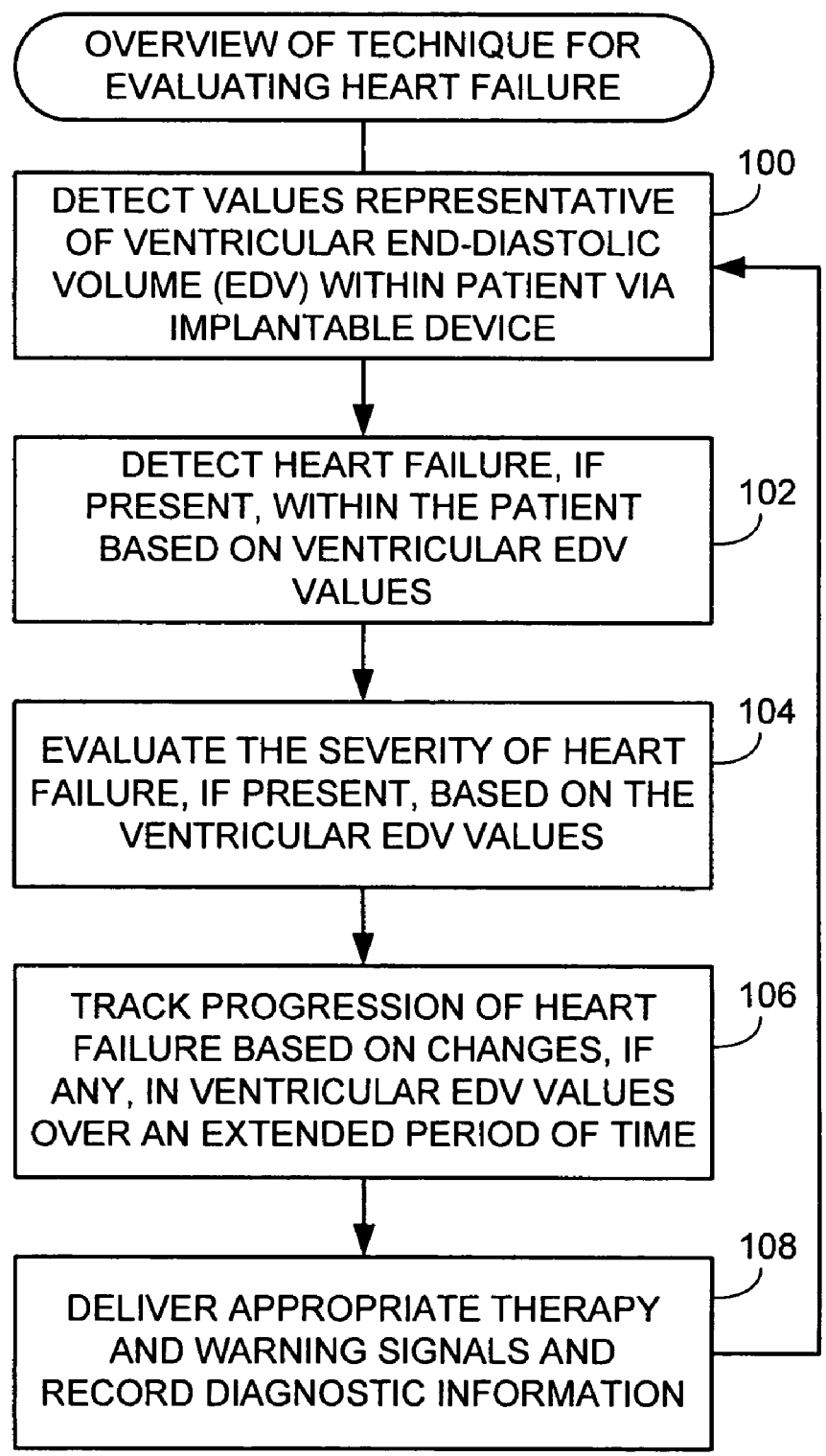
FIG. 2 is a flow diagram providing an overview of the method for evaluating heart failure as performed by the system of FIG. 1.

FIG. 2 summarizes heart failure the evaluation techniques of the invention that may be performed by the system of FIG. 1. Initially, at step 100, the implantable pacer/ICD detects signals representative of ventricular EDV within the patient and, at step 102, detects heart failure, if present, based on the signals. At step, 104, the pacer/ICD evaluates the severity of heart failure based on ventricular EDV values and, at step 106, tracks the progression of heart failure based on changes, if any, in ventricular EDV values over time. At step 108, appropriate therapy and warning signals are delivered and diagnostic data is recorded. As already explained, various types of therapy may be delivered, alone or in combination, depending upon the capabilities of the implanted system. For most patients, the severity of heart failure does not change significantly over short periods of time and so, once a determination has been made as to the current severity of heart failure, this determination need not the repeated, at least in the short-term. Accordingly, from many patients, once the severity of heart failure as been evaluated, it is sufficient to reevaluate the severity of heart failure only infrequently (e.g. every few weeks or months) to determine a change in status of the patient.

Thus, with this technique, ventricular EDV is employed as a proxy for ventricular end diastolic pressure, which is more typically correlated with heart failure. With heart failure, ventricular end diastolic pressure is generally lowered due to a loss in the pumping ability of the ventricles, which results in a decrease in stroke volume and cardiac output. Hence, low ventricular end diastolic pressure within a patient is indicative of heart failure and any decrease in ventricular end diastolic pressure over time is indicative of the progression of heart failure. Likewise, during heart failure, the amount of blood filling the ventricles between the pumping cycles is also diminished. Hence, the maximum volume achieved within the ventricles during a cardiac cycle (i.e. the ventricular EDV) is also representative of heart failure. It is for this reason that ventricular EDV can be used to detect heart failure and to track the progression of heart failure.

Depending upon the particular implementation, either left ventricular EDV, right ventricular EDV or overall ventricular EDV is employed. As noted above, the term ventricular EDV, as it is used herein, refers to any suitable measure of the EDV associated with the ventricles, including right ventricular EDV, left ventricular EDV or combined right and left ventricular EDV. Moreover, ventricular EDV need not be measured at the very end of the diastolic phase of the cardiac cycle. Rather, a value representative of ventricular EDV may be detected, for example, during a pre-ejection period subsequent to a ventricular depolarization (i.e. ventricular volume after active filling), during an interval just prior to an atrial contraction (i.e. ventricular volume after passive filling), or during delivery of a ventricular pacing pulse (V-pulse.) In each case, the ventricles are substantially full and so a measure of the ventricular volume during these intervals can be taken to be representative of ventricular EDV. Typically, left ventricular EDV is about 150 milliliters (ml) and right ventricular EDV is about 165 ml for a healthy, adult heart. Hence, the total ventricular EDV is about 315 ml. If heart failure is occurring, ventricular EDV is typically higher. Note also that the difference between the ventricular volumes after active and passive filling serves as a good indicator of atrial function.

In examples set forth below, combined ventricular EDV is detected based on impedance signals sensed between electrodes implanted in the left and right ventricles. Left ventricular EDV could instead be detected by employing a pair of electrodes implanted within the left ventricles. Likewise, right ventricular EDV could instead be detected by employing pair of electrodes implanted within the right ventricles. By using electrodes implanted within the ventricles, ventricular EDV is determined based upon impedance values derived from an electrical field generally confined to the ventricles and hence substantially unaffected by other factors, such as fluid levels with the lungs. Generally, any suitable measure of ventricular EDV can be employed to detect heart failure and track its progression so long as the technique is consistent, e.g. right ventricular EDV values are not compared against left ventricular EDV values, left ventricular EDV values are not compared against combined ventricular EDV values, etc.

Briefly, using the technique of the invention, heart failure can be detected based upon ventricular EDV by comparing a current value of ventricular EDV (averaged over multiple cardiac cycles) against a threshold value representative of the onset of heart failure. The severity of heart failure can be evaluated by comparing the current ventricular EDV against a table of various threshold values representative of various levels of severity of heart failure, such as those set forth in the NYHA classification scheme. Finally, the progression of heart failure can be tracked by detecting changes, if any, in the average ventricular EDV values over time. Care is taken to detect ventricular EDV at consistent baseline points within multiple cardiac cycles to provide baseline values suitable for comparison purposes.

Figure 3:
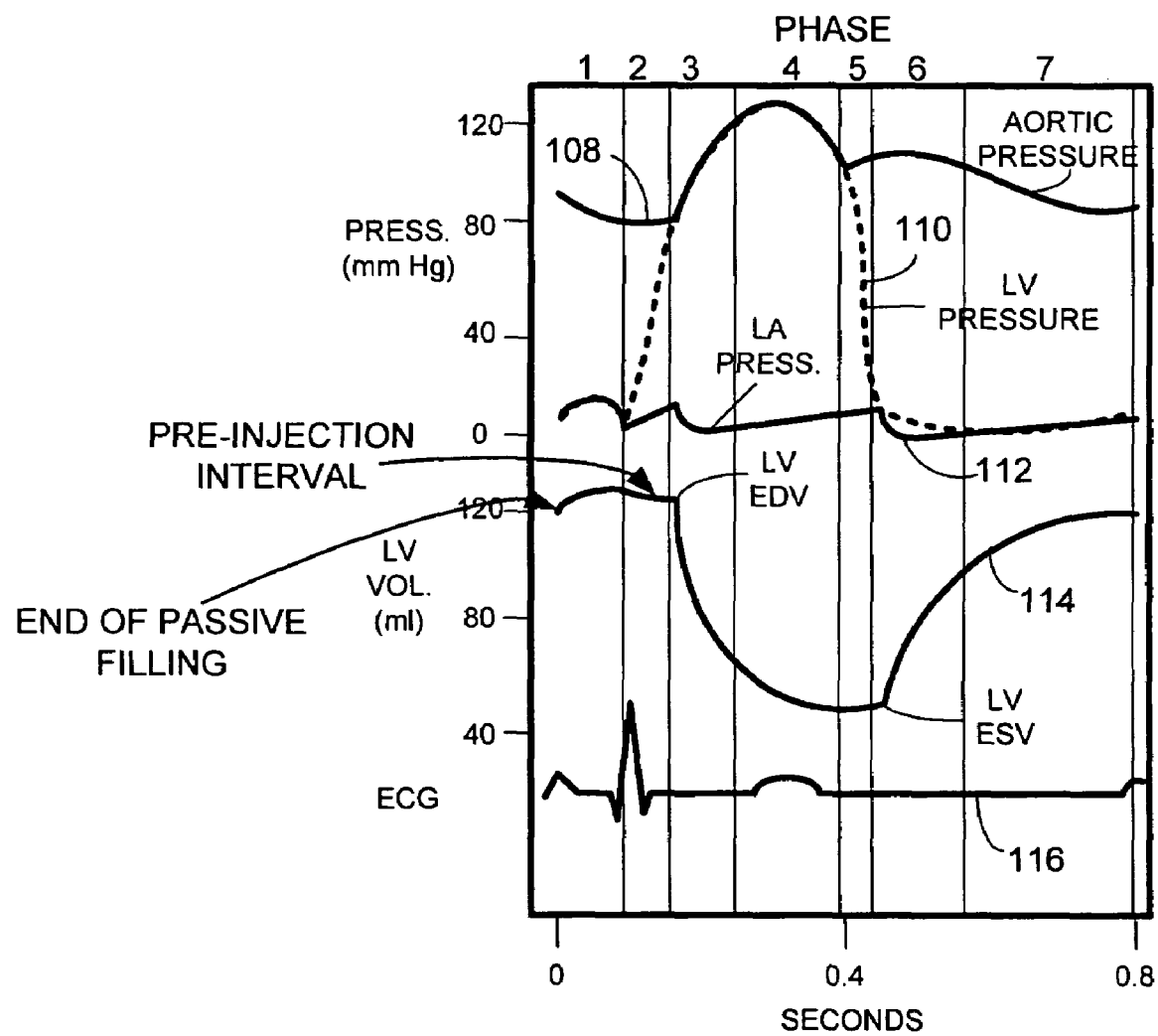
FIG. 3 is a stylized diagram of a cardiac cycle illustrating changes in left ventricular pressure and volume and particularly illustrating left ventricular EDV and left ventricular ESV.

Referring now to FIG. 3, left ventricular pressure, left ventricular EDV, left ventricular ESV and other features of a cardiac cycle will be summarized. More specifically, FIG. 3 is a graph providing stylized representations of aortic pressure 108, left ventricular pressure 110 and left atrial pressure 112. Left ventricular volume 114 is also shown, with left ventricular EDV and left ventricular ESV specifically identified. Additionally, an ECG 116 is shown, which includes stylized representations of a P-wave, R-wave (or QRS complex) and a T-wave. These features are shown over a single cardiac cycle, which is subdivided into seven separate phases, labeled 1-7.

The left ventricular EDV is substantially at its maximum (indicating that the left ventricle is substantially full) during an interval extending from just prior to an atrial contraction (i.e. near the end of phase 7) through a pre-ejection interval (phase 2) to the end of the diastolic phase (i.e. the very end of phase 2), with only relatively minimal variations in volume during this entire interval of time. Accordingly, any measure of ventricular volume during this interval of time is generally representative of the maximum volume achieved by the ventricles and hence is generally representative of EDV. Moreover, during these intervals, the ventricular volume remains substantially constant, i.e. there is little or no change or gradient in volume. Accordingly, this represents an ideal interval of time for detecting ventricular volume values that can be reliably compared from one cardiac cycle to another. In other words, by detecting ventricular volume during intervals wherein there is little or no gradient in the volume, changes in heart rate and cardiac rhythm morphology will not substantially affect the detected values—particularly when averaged over multiple respiration cycles—thus permitting reliable comparison of averaged values of over time. Thus, in one illustrative embodiment, the timing of the ventricular volume measurement can be based on an IEGM signal, such as a following an atrial event or a ventricular event. Also, the system may take a plurality of measurements during each cycle, for example after detecting a suitable IEGM signal, and taking the maximum value as the best representation of the EDV.

As will be explained in more detail below, specific detection windows are defined just prior to atrial contraction and during the pre-ejection interval for use in detecting baseline values of ventricular volume. Low magnitude impedance detection pulses are delivered at the baseline points for use in evaluating ventricular impedance, from which ventricular EDV is derived. Alternatively, ventricular volume can instead be detected during the delivery of a V-pulse. (Although no V-pulse is specifically shown in FIG. 3, the V-pulse would be delivered near the end of phase 1, i.e. shortly before a next expected intrinsic ventricular depolarization.) By detecting ventricular volume using a V-pulse, separate impedance detection pulses need not be generated, thus saving device power.

Although FIG. 3 only specifically illustrates left ventricular volume, right ventricular volume and combined left and right ventricular volume exhibit similar variations over the cardiac cycle and so the comments provided above with respect to left ventricular volume are equally applicable to the right ventricular volume and to the combined left and right ventricular volume.

Thus, FIG. 3 provides an overview of the heart failure evaluation techniques of the invention. In the following section, an exemplary pacer/ICD will be described, which includes specific components for performing the heart failure evaluation technique of FIG. 3.

Pacer/ICD

Figure 5:
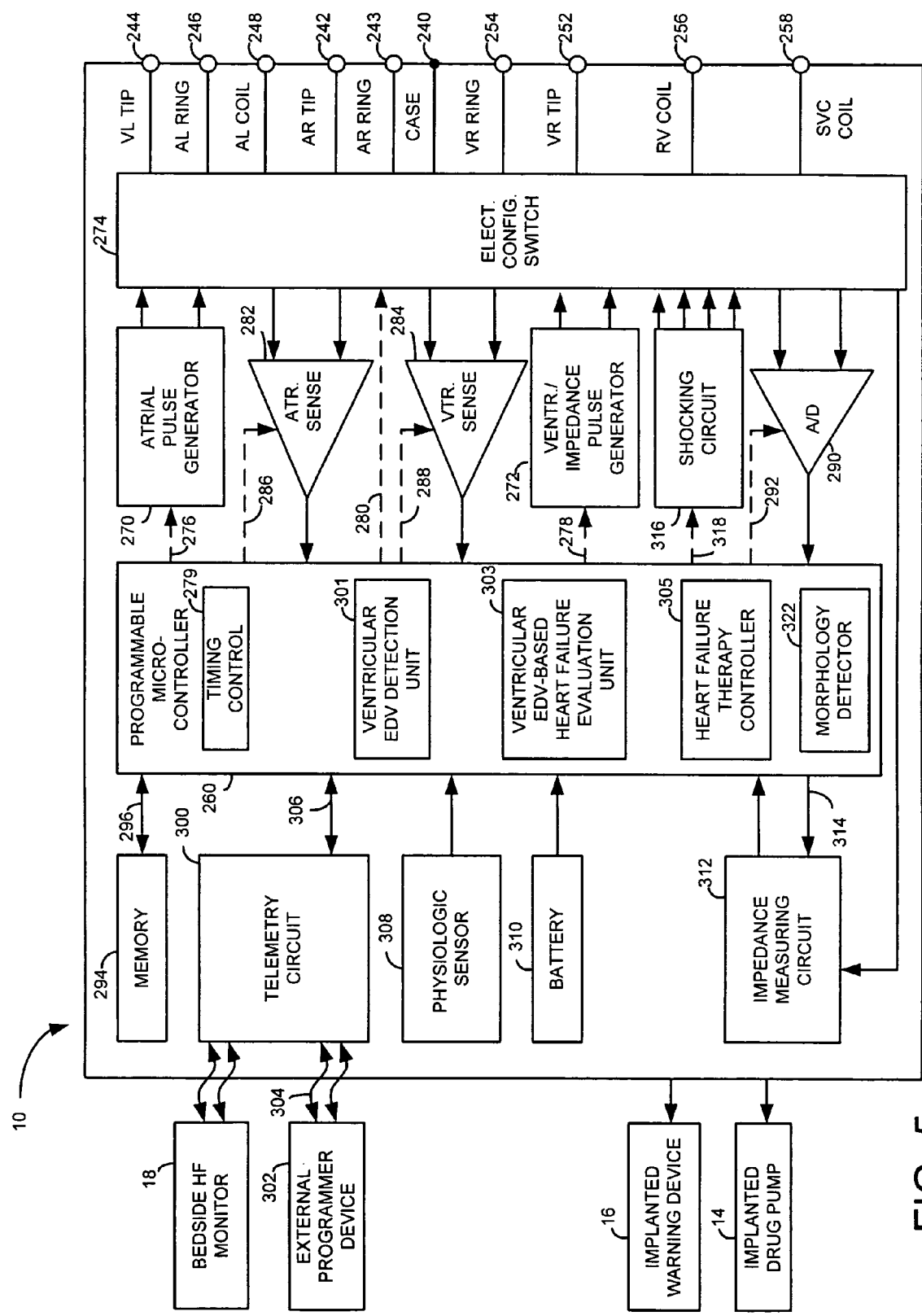
FIG. 5 is a functional block diagram of the pacer/ICD of FIG. 4, illustrating basic circuit elements that provide cardioversion, defibrillation and/or pacing stimulation in the heart and particularly illustrating components for detecting heart failure and tracking its progression and for controlling delivery of therapy or warning signals in response thereto.

With reference to FIGS. 4 and 5, a detailed description of the pacer/ICD of FIG. 1 will now be provided. FIG. 4 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto.

To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 5. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 240 for pacer/ICD 10, shown schematically in FIG. 5, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal (A$_L$ RING) 246, and a left atrial shocking terminal (A$_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal (V$_R$ TIP) 252, a right ventricular ring terminal (V$_R$ RING) 254, a right ventricular shocking terminal (R$_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 5, an atrial pulse generator 270 and a ventricular/impedance pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses. Pulse generator 272 is also used to deliver low magnitude ventricular impedance detection pulses for use in detecting ventricular EDV for heat failure evaluation purposes. Preferably the impedance detection pulses are generated by connecting pulse generator 272 to V$_L$ tip terminal 244 and V$_R$ tip 252 terminal for delivering the pulses between V$_L$ tip electrode 226 and V$_R$ tip electrode 232 (FIG. 4.)

The microcontroller 260 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart. Ventricular sense circuit 282 is also used to sense the low magnitude impedance detection pulses for use in evaluating ventricular EDV for heat failure evaluation purposes.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. Pacer/ICD 10 further includes an accelerometer or other physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states) and to detect arousal from sleep. Accordingly, the microcontroller 260 responds by adjusting the various pacing parameters (such as rate, AV Delay, V-V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor incorporating an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 310, which provides operating power to all of the circuits shown in FIG. 5. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and appropriate batteries.

As further shown in FIG. 5, pacer/ICD 10 is shown as having an impedance measuring circuit 312 which is enabled by the microcontroller 260 via a control signal 314. Herein, impedance is primarily detected for use in evaluating ventricular EDV but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5-10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes various components directed to the controlling the detection and treatment of heart failure. More specifically, the microcontroller includes a ventricular EDV detection unit 301, a ventricular EDV-based heart failure evaluation unit 303 and a heart failure therapy controller 305, which will be described in detail with reference to FIG. 6. Depending upon the implementation, the various components of the microcontroller may be implemented as separate software modules. The modules may be combined to permit a single module to perform multiple functions. In addition, although shown as being sub-components of the microcontroller, some or all of these components may be implemented separately from the microcontroller.

Exemplary Heart Failure Evaluation and Tracking Components

Figure 6:
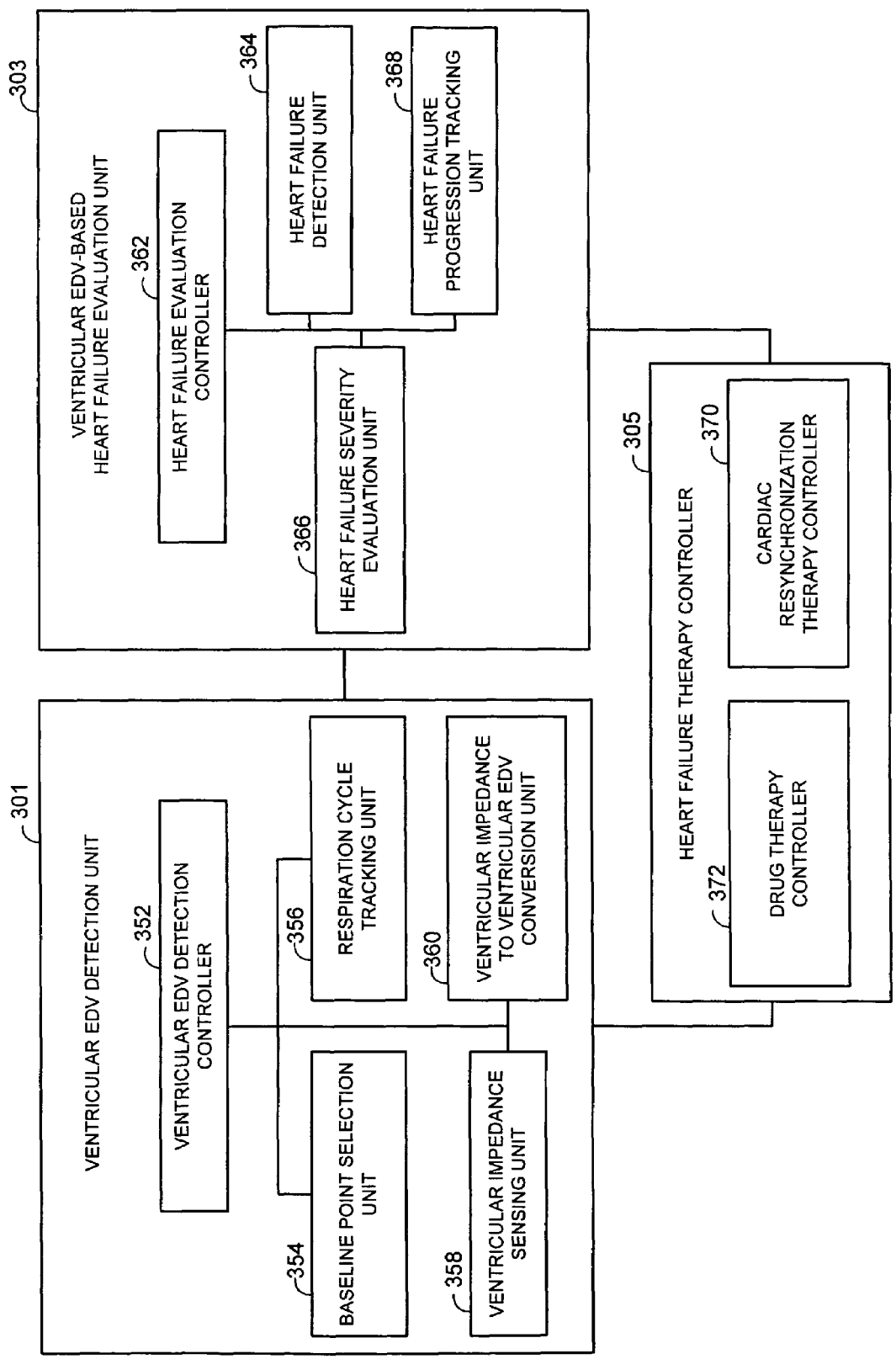
FIG. 6 is a functional block diagram of selected components of the microcontroller of the pacemaker or ICD of FIG. 5, particularly illustrating internal components of a ventricular EDV detection unit, a ventricular EDV-based heart failure evaluation unit and a heart failure therapy controller.

Pertinent functional components of an exemplary ventricular EDV detection unit 301, ventricular EDV-based heart failure evaluation unit 303, and heart failure therapy controller 305 are shown in FIG. 6. Briefly, the ventricular EDV detection unit includes a detection controller 352 that coordinates the detection and tracking of the ventricular EDV. To this end, the detection controller activates a baseline point selection unit 354 that identifies a consistent point within each cardiac cycle for detecting the ventricular EDV to eliminate any modulation caused by the heart beating. The baseline point is preferably during an interval just prior to an atrial contraction or during the pre-ejection interval or is instead contemporaneous with delivery of a V-pulse. The controller also activates a respiration cycle tracking unit 356 that tracks respiration (typically via changes in thoracic impedance) to permit ventricular EDV values to be detected and averaged over at least one complete respiration cycle to eliminate any modulation caused by respiration. In any case, once a baseline point has been identified (and various techniques for identifying appropriate baseline points are set forth below), a ventricular impedance sensing unit 358 is activated, which senses the impedance between at least two ventricular electrodes using either an impedance detection pulse or a V-pulse. Once the ventricular impedance is sensed, a ventricular impedance to ventricular EDV conversion unit 360 converts to the impedance value to a volume value in a manner set forth below. The ventricular EDV detection controller processes of the ventricular EDV values detected over one or more respiration cycles to generate an averaged value for comparison purposes.

Depending upon the implementation, the ventricular EDV values may be averaged over individual respiration cycles or may be averaged over an entire day or week, as specified by device programming, so as to generate a suitable averaged value for use in tracking small changes in ventricular EDV over time. The use of consistent baseline values helps eliminate changes in ventricular EDV caused by changes in heart rate or cardiac rhythm morphology. Additionally, ventricular EDV values may be detected only when the heart rate of the patient is within certain predetermined range to further reduce variations caused by heart rate. In addition, preferably, the device is configured to detect and average ventricular EDV values only during periods of time when R-R intervals are substantially uniform and when no arrhythmias are occurring so that cardiac rhythm abnormalities caused by an arrhythmia do not adversely affect the evaluation of the ventricular EDV. Alternatively, ventricular EDV may be detected only, for example, while the patient is sleeping. As can be appreciated, a wide variety of techniques may be employed for isolating particular circumstances for detecting and averaging ventricular EDV values for use in evaluating heart failure. Routine experimentation may be employed to identify particular circumstances that are most effective for use in detecting and averaging ventricular EDV values so that heart failure may be reliably tracked thereby.

In any case, once a suitable measure of the ventricular EDV has been obtained by the EDV detection unit, ventricular EDV-based heart failure evaluation unit 303 uses the ventricular EDV to detect and evaluate heart failure, if present, within the patient. To this end, the evaluation unit includes an evaluation controller 362 that selectively controls a heart failure detection unit 364, a heart failure severity evaluation unit 366 and a heart failure progression tracking unit 368. In one example, the heart failure detection unit compares the ventricular EDV of the patient against a volume-based threshold value indicative of the onset of heart failure and, if the ventricular EDV for the patient rises above the threshold, heart failure is thereby detected, therapy is initiated, alarm or warning signals are generated, and appropriate diagnostic information is recorded. Preferably, the detection of heart failure requires that the average ventricular EDV consistently exceed the threshold over an extended period time, such as a week, so that an indication of heart failure is not improperly generated due to transient events occurring within the patient. Note that if ventricular EDV is represented in terms of an impedance value rather than a volume value, then the impedance value must fall below an impedance-based threshold value before heart failure is detected. This is because a smaller impedance value is representative of a larger ventricular EDV.

The threshold value for detecting heart failure may be a programmed value specified by the physician based, in part, on an evaluation of the physical characteristics of the patient, such as age, size, weight, gender and the like. Thus, in a hypothetical example, if the patient is in adult, male, of fairly average size, a value of 335 ml may be found to be the appropriate volume-based threshold value. Hence, if the ventricular EDV for the patient rises above that value, heart failure is thereby detected. Actual threshold values for various categories of patients may be derived from otherwise routine experimental studies of ventricular EDV for populations of patients of differing sizes, ages, genders, and the like for use in programming the implantable device. Alternatively, assuming the patient does not have heart failure at the time of implant, the physician may determine the ventricular EDV for the patient, then set the volume-based threshold value somewhere above that value. As another alternative, detection of heart failure is made based on some combination of ventricular EDV values and other detected parameters of the patient. For example, if a sensor is provided for evaluating stroke volume, a detection of heart failure is only made if high ventricular EDV values are corroborated by detection of relatively low stroke volume.

Assuming that heart failure is detected, then heart failure evaluation controller 362 activates severity evaluation unit 366 to determine the severity of heart failure and also activates progression tracking unit 368 to track changes in heart failure, if any, over time. The severity of heart failure may be evaluated by comparing the ventricular EDV for the patient against a set of separate threshold values representative of different levels of severity of heart failure. Again, such threshold values may be set by the physician based on an evaluation of the physical characteristics of the patient in combination with clinical data obtained for various categories of patients via otherwise routine experimental studies. Alternatively, assuming the patient does not have heart failure at the time of implant, the physician may determine the initial ventricular EDV for the patient, then set the volume-based severity threshold values based on that initial value. As can be appreciated, a wide variety of techniques may be used for setting the various threshold values for use with the invention.

Heart failure progression tracking unit 368 stores the current value for the ventricular EDV for the patient for comparison against additional values detected and recorded in the future to permit tracking of the progression of heart failure. For example, ventricular EDV values may be calculated and stored once every month so that any changes in heart failure from month-to-month can be detected and appropriate diagnostic data stored. In particular, if a significant increase in heart failure occurs from one month to another, or perhaps from one week to another, warning signals are generated advising the patient to see his or her physician as soon as possible. Insofar as progression tracking is concerned, the device need only compare the ventricular EDV values for the patient detected at various times and need not compare the values against any predetermined threshold values. In other words, only changes in the ventricular EDV values are pertinent, the absolute magnitude of those values is not pertinent. Depending upon the implementation, the implanted device may be provided only with the heart failure progression tracking capability without heart failure detection or evaluation capability. This may be appropriate, for example, for use in patients who are already known to have heart failure so that heart failure detection is not necessary. Within such patients, it may be sufficient merely to detect any changes in heart failure with time.

In addition, depending upon the implementation, the device need not convert ventricular impedance values to ventricular EDV values. Rather, it is sufficient to detect changes in ventricular impedance values over time. Any significant decrease in ventricular impedance is indicative of a worsening of heart failure. Likewise, insofar as detecting the onset of heart failure or for evaluating its severity, ventricular impedance values may be compared directly against impedance-based threshold values. Routine experimentation may be employed to define suitable impedance-based threshold values.

Finally, with respect to FIG. 6, assuming heart failure is detected, heart failure therapy controller 303 is activated to deliver appropriate therapy to address and hopefully mitigate the heart failure. To this end, a CRT controller 370 is activated to control delivery of CRT therapy to the heart of the patient to improve cardiac function. If an implanted drug pump is provided, a drug therapy controller 370 is activated to the deliver appropriate medications directly into the bloodstream of patient. These therapies will be discussed in detail below. Any improvement in heart failure resulting from the administration of therapy can be tracked and appropriate diagnostic information stored for subsequent review by the physician. The heart therapy controller may adjust or titrate therapy based upon the severity of heart failure as detected by severity evaluation unit 366. Hence, if heart failure is still relatively mild, perhaps only CRT therapy is provided. If the heart failure becomes more severe, then more aggressive CRT may be employed along with appropriate drug therapy. Note that the delivery of therapy, if effective, will likely decrease ventricular EDV. Hence, care should be taken when comparing ventricular EDV values detected before therapy and after therapy.

Thus, FIG. 6 summarizes exemplary internal functional components of ventricular EDV detection unit 301, ventricular EDV-based heart failure evaluation unit 303 and heart failure therapy controller 305. Depending upon the implementation, the components may be configured as separate software or hardware modules. The modules may be combined to permit single modules to perform multiple functions.

Figure 7:
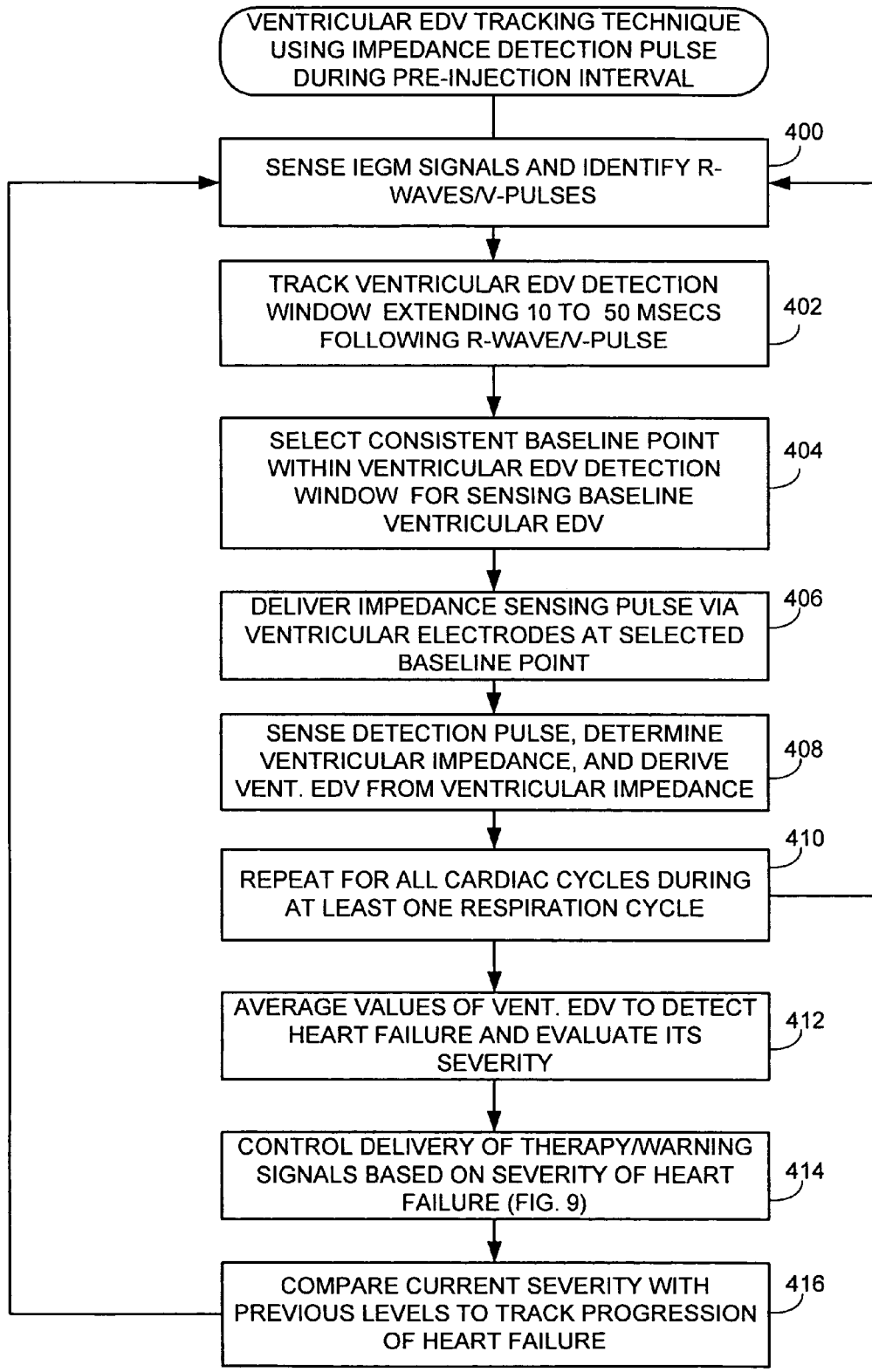
FIG. 7 is a flow diagram illustrating an exemplary method performed by the implanted system of FIGS. 4-6 for evaluating heart failure based on ventricular EDV, which employs a low voltage impedance measuring pulse delivered to the ventricles during a pre-ejection interval.

Exemplary Heart Failure Evaluation Technique Using Impedance Detection Pulse During Pre-ejection Interval Various examples of heart failure evaluation techniques that may be performed using the systems described above are set forth in the remaining figures. Referring first to FIG. 7, a technique is described wherein impedance detection pulses are delivered during pre-ejection intervals for detecting ventricular EDV. Initially, at step 400, the ventricular EDV detection unit of the implanted device senses internal electrocardiogram (IEGM) signals and identifies R-waves and V-pulses. R-waves are detected by sensing ventricular depolarization using otherwise conventional techniques. V-pulses, which are generated by the implanted device itself, need not be detected. Rather, data identifying the point in time for delivery of a V-pulse is merely forwarded from pacing control components of the microcontroller to the ventricular EDV detection unit. In any case, at step 402, the ventricular EDV detection unit tracks a detection window for detecting ventricular EDV, which extends from 10 to 50 milliseconds following the peak of the latest R-wave or V-pulse, i.e. the detection window covers a portion of the pre-ejection interval between the ventricular depolarization of the R-wave/V-pulse and the end of the diastolic phase of the cardiac cycle when the ventricles begin to eject blood. An exemplary pre-ejection interval detection window 403 is shown within FIG. 8 along with a stylized IEGM signal 405. Next, at step 404, the ventricular EDV detection unit selects a baseline point within the detection window for use in sensing a baseline ventricular EDV value. The baseline point may be set anywhere within the detection window. Preferably, however, the location of the baseline point is consistent from one beat to the next. By setting the baseline point consistently within the sensing window, a more reliable evaluation of ventricular EDV is thereby obtained. In one example, the baseline point is simply set to be midway between the beginning and the end of the detection window, i.e. at a point 30 milliseconds following the peak of the R-wave or V-pulse. The location of the baseline point within the selection window may be a programmable parameter.

Next, at step 406, the ventricular EDV detection unit controls pulse generator 272 (FIG. 5) to deliver a low magnitude impedance sensing pulse to the heart of the patient at the selected baseline point. An exemplary low magnitude pulse is 407 is shown in FIG. 8. Preferably, the magnitude of the pulse is set as low as possible while still being sufficiently strong to allow the impedance of the ventricles to be sensed using the pulse. Pulse magnitudes may be in the range or, for example, 100 micro amperes (mA) to 1 mA. By using a low magnitude pulse, battery drain is reduced. Moreover, the use of a low magnitude pulse minimizes the risk that the pulse may inadvertently depolarize portions of the cardiac muscle. Although the ventricles are likely to be refractive during the pre-ejection interval, the atria may no longer be refractive at that point and hence may be vulnerable to inadvertent depolarization caused by propagation of the detection pulse into the atria, if its magnitude were set too high.

At step 408, the ventricular EDV detection unit senses the detection pulse via ventricular sense amplifiers 284 (FIG. 5) and determines ventricular impedance from the sensed pulse using otherwise conventional techniques. Impedance detection techniques are set forth in U.S. Pat. No. 5,861,008 to Obel et al., entitled "Heart Stimulating Device With Stimulation Energy Responsive To Detected Noise", which is incorporated by reference herein. In addition, at step 408, the ventricular impedance value is converted to a ventricular EDV value. Techniques for converting intracardiac impedance values to cardiac chamber volume values are discussed in U.S. Pat. No. 4,674,518 to Salo, entitled "Method and Apparatus for Measuring Ventricular Volume", which is also incorporated by reference herein.

Step 400-408 are repeated for each cardiac cycle during at least one complete respiration cycle, as set forth in the step 410. Once ventricular impedance values have been sensed throughout an entire respiration cycle then step 412 is performed wherein the ventricular EDV values derived from the impedance values are averaged together by the heart failure evaluation unit 303 (FIG. 5) for comparison against the aforementioned threshold values to detect heart failure and evaluate its severity. Assuming heart failure has been detected then, at step 414, heart failure therapy controller 305 (also FIG. 5) controls delivery of therapy and generation of appropriate warning and diagnostic signals based, in part, on the severity of heart failure. Finally, at step 416, the current severity of heart failure of the patient is compared against previous values, if any, already detected for the patient to permit tracking of the progression of heart failure over time. As already noted, appropriate warning and diagnostic signals may be generated in the event there is a significant or sudden progression in the disease. The steps of FIG. 7 are preferably performed periodically, usually once a week or once a month, to permit tracking of the progression of heart failure. In addition, as noted, preferably, the steps are performed only while the patient is at rest (e.g. while the patient is asleep) or otherwise has a stable heart rate to provide ventricular EDV values that can be most reliably compared over extended periods of time.

Figure 9:
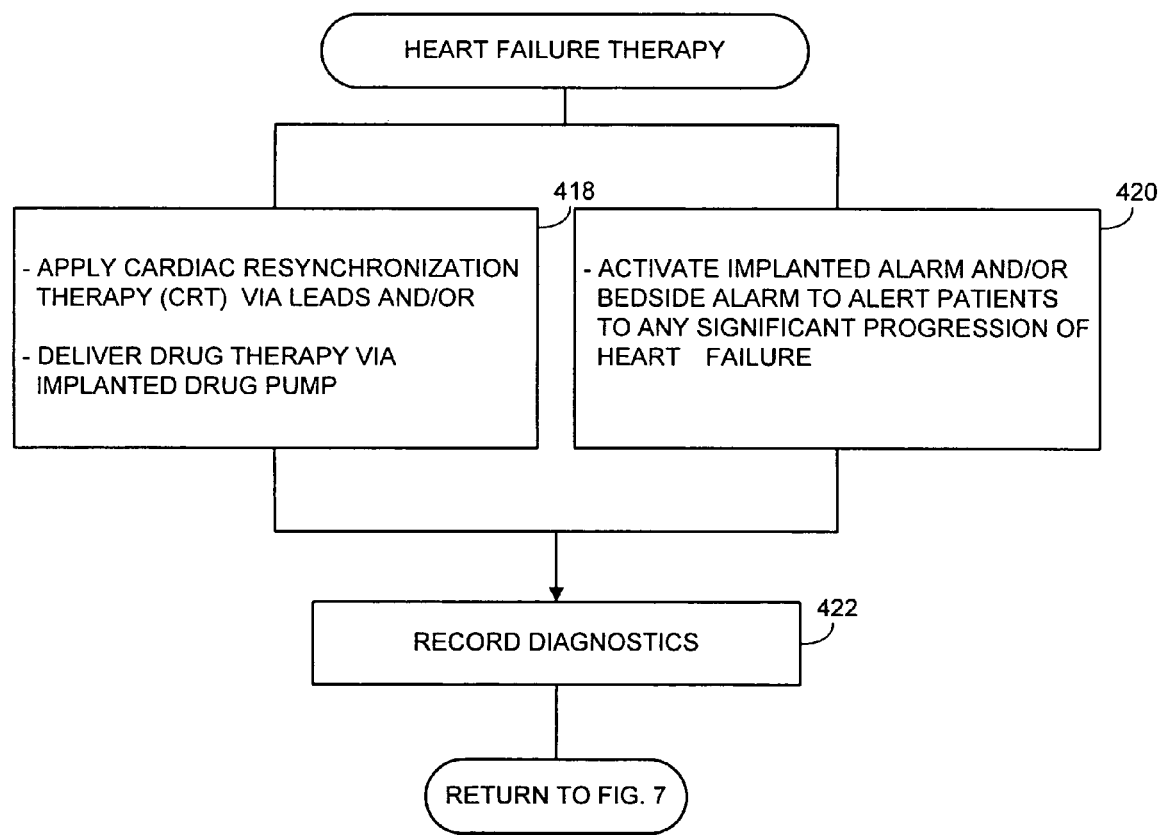
FIG. 9 is a flow diagram illustrating an exemplary method performed by the implanted system of FIGS. 4-6 for delivering therapy and warning signals in response to heart failure.

Referring now to FIG. 9, heart failure therapy, activated at step 414, will be summarized. At step 418, heart failure therapy controller 305 (FIG. 5) controls delivery of CRT and/or drug therapy to the patient. CRT and related therapies are discussed in the above-referenced patents to Mathis et al., Kramer et al., and Stahmann et al. The degree of severity of heat failure may be used to control CRT pacing parameters such as the time delay between left and right ventricular pulses to, for example, provide more aggressive CRT for more severe heart failure.

Drug therapy is delivered using an implanted drug pump, if one is provided. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure. Implantable drug pumps are discussed in U.S. Pat. No. 5,328,460 to Lord et al., entitled "Implantable Medication Infusion Pump Including Self-Contained Acoustic Fault Detection Apparatus", which is incorporated by reference herein.

Simultaneously, at step 420, the heart failure therapy controller may activate the implanted warning device or the bedside monitor, or both, to alert the patient to a significant progression in heart failure. The aforementioned patent to Lord et al. also discusses implantable "tickle" warning devices. As noted above, the bedside monitor may be directly networked with a centralized computing system for immediately notifying the physician of a significant increase in heart failure severity. A system incorporating bedside monitoring units connected to a centralized external programmer system is described in U.S. Pat. No. 6,622,045 to Snell et al., "System And Method For Remote Programming Of Implantable Cardiac Stimulation Devices." At step 422, appropriate diagnostic information is stored within the memory 294 (FIG. 5) of the device for subsequent transmission to external programmer during a follow-up session with the patient for review by a physician or for immediate transmission via the bedside monitor to the centralized computing system, is one is provided.

Figure 10:
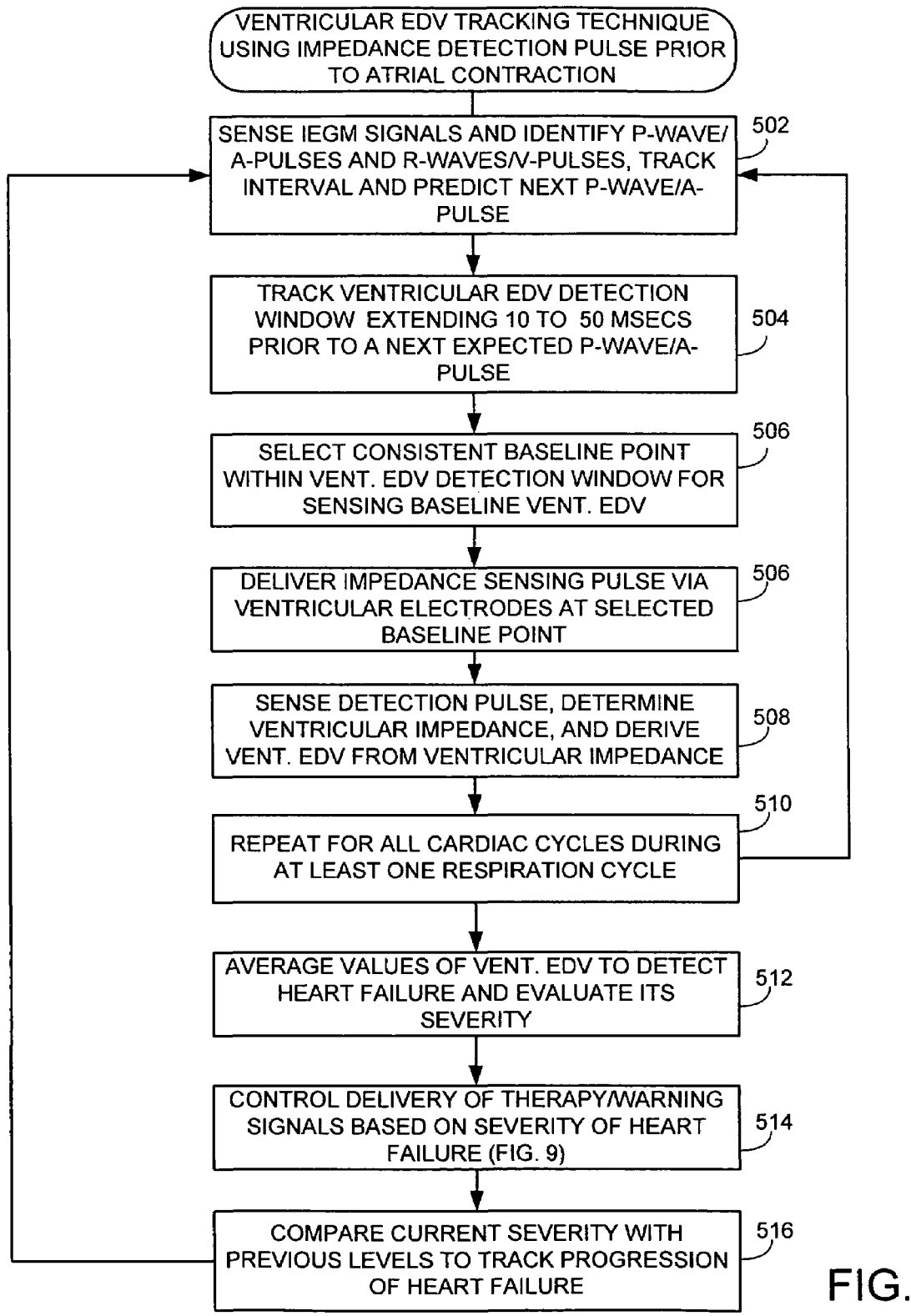
FIG. 10 is a flow diagram illustrating an exemplary method performed by the implanted system of FIGS. 4-6 for evaluating heart failure based on ventricular passive filling measurement, which employs a low voltage impedance measuring pulse delivered to the ventricles just prior to a next expected P-wave/A-pulse.

Exemplary Heart Failure Evaluation Technique Using Impedance Detection Pulse Prior to Atrial Contraction Referring now to FIG. 10, an alternative technique is described wherein impedance detection pulses are delivered during intervals just prior to atrial contractions for detecting ventricular EDV. The technique of FIG. 10 is similar to that of FIG. 7 and only pertinent differences will be described in detail. At step 500, IEGM signals are sensed and P-waves/A-pulses and R-waves/V-pulses are identified. In addition, at step 500, the interval between R-waves/V-pulses and subsequent P-waves/A-pulses is tracked and the timing of a next expected P-wave/A-pulse is predicted. The timing of P-waves is detected based on the sensed interval between R-waves and P-waves. A-pulses, which are generated by the implanted device itself, need not be detected. Rather, timing data identifying the point in time for delivery of a next A-pulse is merely forwarded from pacing control components of the microcontroller to the ventricular EDV detection unit. In any case, at step 502, a detection window is tracked, which extends 10 to 50 milliseconds before the next expected P-wave or A-pulse. An exemplary detection window 503 is shown within FIG. 11 along with a stylized IEGM signal 505.

At step 504, a baseline point is selected within the detection window for use in sensing a baseline ventricular EDV value. As before, the baseline point may be set anywhere within the detection window but is preferably set consistently from one beat to the next. In one example, the baseline point is set 30 milliseconds prior to a next expected P-wave/A-pulse. Next, at step 506, a low magnitude impedance sensing pulse is delivered at the selected baseline point. An exemplary low magnitude pulse is 507 is shown in FIG. 11. The use of a low magnitude pulse is particularly important during the interval prior to the atrial contraction, to prevent triggering of either an atrial or ventricular contraction, since neither the atria nor the ventricles are refractory during that interval.

At step 508, the detection pulse is sensed, ventricular impedance is derived therefrom, and the ventricular impedance value is converted to a ventricular EDV value. Steps 500-508 are repeated for each cardiac cycle during at least one complete respiration cycle, as specified by step 510. Then step 512 is performed wherein the ventricular EDV values are averaged for comparison against the aforementioned threshold values to detect heart failure and evaluate its severity. At step 514, heart failure therapy is delivered and appropriate warning and diagnostic signals are generated in accordance with the techniques described in connection with FIG. 9. Finally, at step 516, the current severity of heart failure of the patient is compared against previous values to permit tracking of the progression of heart failure over time.

Figure 12:
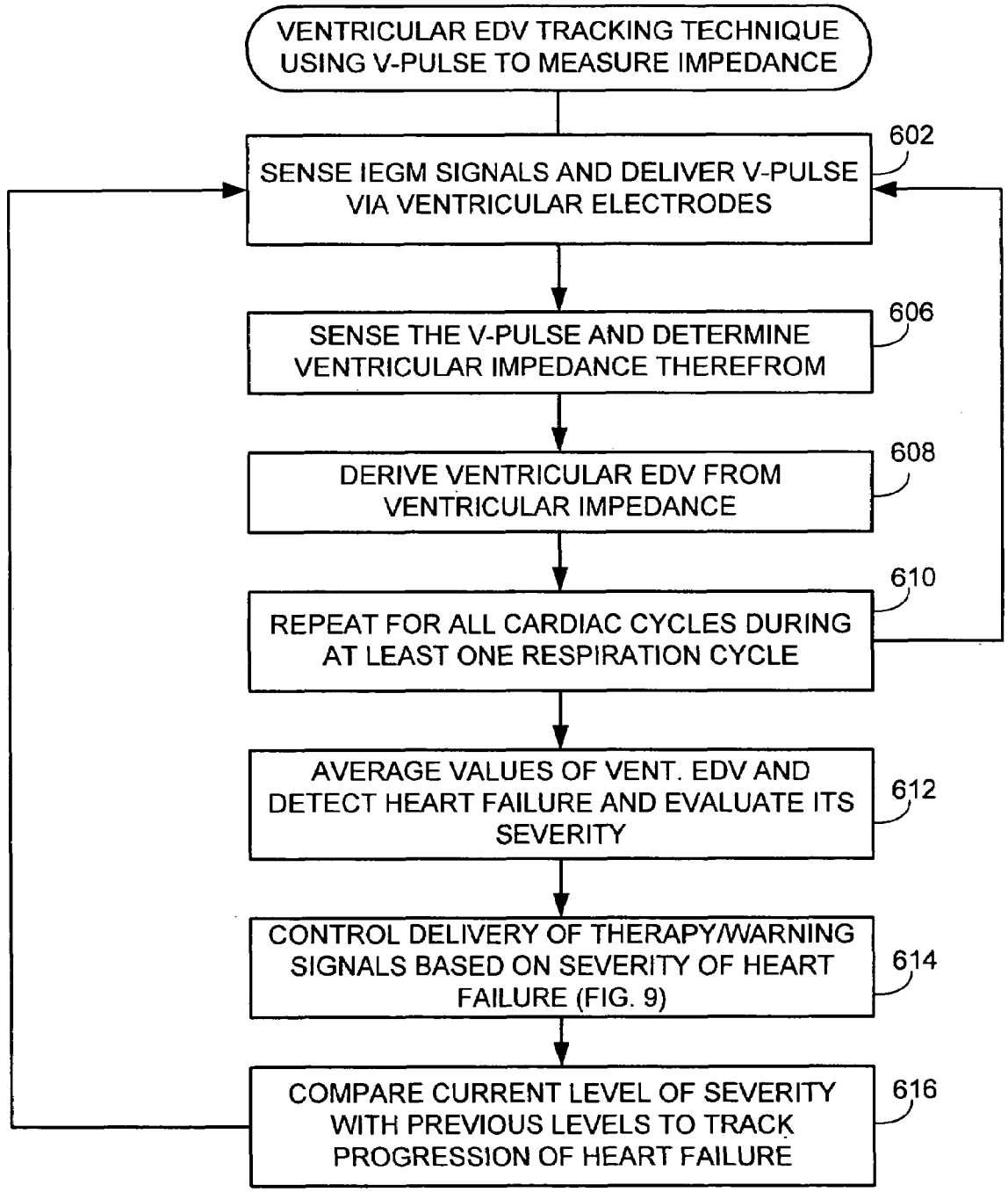
FIG. 12 is a flow diagram illustrating an exemplary method performed by the implanted system of FIGS. 4-6 for evaluating heart failure based on ventricular EDV, which utilizes a V-pulse for measuring ventricular impedance.

Exemplary Heart Failure Evaluation Technique Using V-pulse as Impedance Detection Pulse Referring now to FIG. 12, an alternative technique is described wherein V-pulses are use as impedance detection pulses for detecting ventricular EDV. The technique of FIG. 12 is similar to the above-described techniques and only pertinent differences will be described in detail. At step 600, IEGM signals are sensed and V-pulses are delivered in accordance with conventional ventricular pacing techniques. Exemplary V-pulses 607 are shown within FIG. 11 along with a stylized IEGM signal 605. The use of the V-pulse as the impedance detection pulse provides even further savings in power, particularly if ventricular pacing is to be performed anyway. Then, at step 608, the V-pulse is sensed and ventricular impedance derived therefrom and converted to a ventricular EDV value. Steps 600-608 are repeated for each cardiac cycle during at least one complete respiration cycle, as set forth in the step 610, then step 612 is performed wherein the ventricular EDV values are averaged for comparison against threshold values to detect heart failure and evaluate its severity. At step 614, heart failure therapy is delivered and appropriate warning and diagnostic signals are generated. Finally, at step 616, the current severity of heart failure of the patient is compared against previous values to permit tracking of the progression of heart failure over time.

What have been described are various systems and methods for use with a pacer/ICD for evaluating heart failure and providing therapy and warning signals. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A system for evaluating progression of heart failure within a patient using an implantable medical device, comprising:
    a ventricular end-diastolic volume (EDV) detection unit for detecting values representative of ventricular EDV;
    wherein the system is coupled to at least two electrodes configured for implant within the patient's ventricles and wherein the EDV detection unit is adapted to:

(i.) identify a baseline point in time within each of a plurality of cardiac cycles for detecting the values representative of ventricular EDV, wherein the baseline point in time within each of the plurality of cardiac cycles is identified by tracking a pre-ejection interval and then selecting a point in time within the pre-ejection interval;

(ii.) detect a signal representative of an impedance between the two ventricular electrodes at each baseline point in time; and (iii.) determine a baseline ventricular EDV value based on the impedance signal detected at each baseline point in time; and wherein the system further comprises a ventricular EDV-based heart failure evaluation unit operative to detect progression of heart failure within the patient based on detecting changes, if any, over time in the baseline ventricular EDV values.

2. The system of claim 1 and further comprising:
a heart failure therapy controller that is responsive to detection of a progression of heart failure by the heart failure evaluation unit to adjust one or more operating parameters.

3. The system of claim 2 wherein the heart failure therapy controller is further adapted to deliver cardiac resynchronization therapy (CRT) to the heart of the patient.

4. The system of claim 1 and further comprising:
an implantable drug pump in communication with the heart failure evaluation unit and responsive to detection of a progression of heart failure by the heart failure evaluation unit to administer a drug.

5. The system of claim 1 and further comprising:
an implantable heart failure warning device in communication with the heart failure evaluation unit and responsive to detection of a progression of heart failure by the heart failure evaluation unit to generate a warning.

6. The system of claim 1 wherein the EDV detection unit is further adapted to detect the values representative of ventricular EDV during a ventricular pacing pulse.

7. The system of claim 1 wherein the heart failure evaluation unit is further adapted to detect heart failure by comparing the values representative of the ventricular EDV of the patient against a threshold ventricular EDV value indicative of heart failure.

8. The system of claim 1 wherein the heart failure evaluation unit is further adapted to evaluate the severity in heart failure, if present, within the patient based on the values representative of ventricular EDV.

9. The system of claim 8 wherein the heart failure evaluation unit is adapted to evaluate the severity in heart failure by comparing the values representative of the ventricular EDV of the patient against various threshold ventricular EDV values indicative of various degrees of heart failure.

10. The system of claim 1 wherein the heart failure evaluation unit is further adapted to detect changes in heart failure within the patient based on determining changes, if any, over time in the values representative of ventricular EDV.

11. The system of claim 10 wherein the heart failure evaluation unit is further adapted to detect changes in heart failure by comparing the values representative of ventricular EDV detected over an extended period of time.

12. The system of claim 11 wherein the heart failure evaluation unit is further adapted to compare values representative of ventricular EDV detected over a period of at least one month.

13. The system of claim 1 wherein the EDV detection unit is further adapted to detect values representative of ventricular EDV by:

tracking at least one respiration cycle;
detecting values representative of ventricular EDV at like baseline points within a plurality of cardiac cycles during the respiration cycle; and
processing the values representative of ventricular EDV over at least one respiration cycle to generate an average ventricular EDV value.

14. The system of claim 13 wherein the EDV detection unit is further adapted to process the values by averaging the values.

15. The system of claim 13 wherein the EDV detection unit is further adapted to average the values over many cardiac cycles to reduce respiratory variation of the EDV value.

16. The system of claim 1 wherein the EDV detection unit is adapted to detect a signal representative of impedance by delivering a detection pulse to the ventricles using the ventricular electrodes at the baseline point and sensing ventricular impedance based on the detection pulse using the ventricular electrodes.

17. The system of claim 16 wherein the EDV detection unit is adapted to select an amplitude of the detection pulse to be sufficiently low to avoid triggering myocardial depolarization.

18. The system of claim 1 wherein the EDV detection unit is adapted to track the pre-ejection interval by:
identifying a ventricular depolarization event; and
identifying a window 10-50 milliseconds (msecs) following the ventricular depolarization event.

19. The system of claim 1 wherein the EDV detection unit is additionally adapted to detect values representative of passive filling volume by:
identifying a baseline point within a cardiac cycle for detecting the value representative of passive filling volume;
detecting a signal representative of the impedance between the two ventricular electrodes at each baseline point in time; and
determining a baseline passive filling volume value based on the impedance signal detected at each baseline point in time.

20. The system of claim 19 wherein the EDV detection unit is adapted to identify the baseline point within the cardiac cycle for detecting the value representative of passive filling volume by:
tracking atrial depolarization to ventricular depolarization intervals during cardiac cycles;
predicting a next expected atrial depolarization based upon the atrial depolarization to ventricular depolarization intervals; and
identifying a window 10-50 milliseconds (msecs) prior to a next expected atrial depolarization.

21. The system of claim 20 wherein the EDV detection unit is adapted to identify the baseline point within the cardiac cycle for detecting the value representative of passive filling volume by identifying the time for delivery of a ventricular pacing pulse.

22. The system of claim 21 wherein the EDV detection unit is adapted to detect the signal representative of the impedance by:
delivering the ventricular pacing pulse using the ventricular electrodes; and
sensing ventricular impedance based upon the ventricular pacing pulse using the ventricular electrodes.

23. A system for tracking progression of heart failure within a patient using an implantable medical device, comprising:

means for determining ventricular end-diastolic volume (EDV) values;

wherein the means for determining ventricular EDV values is coupled to at least two electrodes configured for implant within the patient's ventricles and comprises:

(i.) means for identifying a baseline point in time within each of a plurality of cardiac cycles for detecting the ventricular EDV values, wherein the baseline point in time within each of the plurality of cardiac cycles is identified by tracking a pre-ejection interval and then selecting a point in time within the pre-ejection interval;

(ii.) means for detecting a signal representative of an impedance between the at least two ventricular electrodes at each baseline point in time; and (iii.) means for determining a baseline ventricular EDV values based on the impedance signal detected at each baseline point in time; and wherein the system further comprises means for tracking progression of heart failure, if any, within the patient based on detecting changes, if any, over time in the baseline ventricular EDV values.

24. The system of claim 23 and further comprising:

means for controlling delivery of therapy based on progression of heart failure with the patient.

25. The system of claim 23 and further comprising:

means for administering a drug based on progression of heart failure with the patient.

26. The system of claim 23 and further comprising:

means for generating a warning based on progression of heart failure within the patient.

* * * * *